United States Patent [19]

Jones et al.

[11] 4,303,652

[45] Dec. 1, 1981

[54] FIBER-REACTIVE PHOSPHORUS MOTHPROOFING AGENTS

[75] Inventors: Francis W. Jones; Robert J. Mayfield; Gary J. O'Loughlin, all of Geelong, Australia

[73] Assignee: Commonwealth Scientific and Industrial Research Organization, Australia

[21] Appl. No.: 938,253

[22] Filed: Aug. 30, 1978

[30] Foreign Application Priority Data

Sep. 6, 1977 [AU] Australia .................... PD1533

[51] Int. Cl.$^3$ .................. A61K 31/41; A61K 31/675; C07D 249/12; C07F 9/65
[52] U.S. Cl. ..................... 424/200; 260/949; 260/952; 544/232; 544/235; 544/237; 544/243; 544/244; 544/195; 544/214; 548/116; 548/118; 424/216; 424/218; 8/128 R
[58] Field of Search .............. 260/949, 952; 548/118, 548/11 V, 116; 424/200, 216, 218; 8/128 R; 544/232, 235, 237, 243, 191, 244, 214

[56] References Cited

U.S. PATENT DOCUMENTS

| | | | |
|---|---|---|---|
| B 534,591 | 2/1976 | Beriger | 260/948 |
| 3,419,620 | 12/1968 | Becher et al. | 260/952 |
| 3,904,710 | 9/1975 | Oswald | 260/949 |
| 4,067,972 | 1/1978 | Oswald | 424/216 |
| 4,119,715 | 10/1978 | Hoffmann | 424/216 |

*Primary Examiner*—Anton H. Sutto
*Attorney, Agent, or Firm*—Bacon & Thomas

[57] ABSTRACT

Organophosphorus esters, useful in increasing the resistance of keratinous materials to attack by keratin-eating insects, have the general formula:

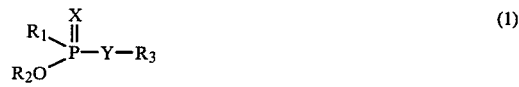

(1)

wherein:
X and Y are independently O or S;
$R_1$ is an alkyl, alkoxy, alkylamino, dialkylamino or alkylmercapto radical having 1 to 6 carbon atoms; an amino or aryl radical;
$R_2$ is an alkyl radical having 1 to 6 carbon atoms;
$R_3$ is a radical of the general formula:

$$-J-(K-L)_n \qquad (2)$$

wherein:
J is an aliphatic radical, or radical containing an aromatic or heterocyclic ring;
K is one of the following radicals:

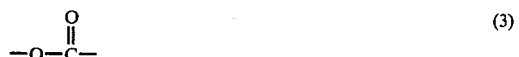

(3)

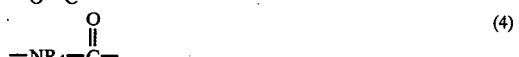

(4)

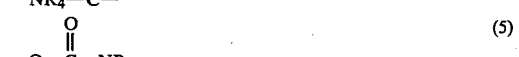

(5)

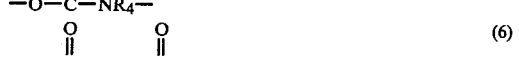

(6)

—O—   (7)

linked to J through the oxygen atom in the case of (3), (5) or (6), and through the nitrogen atom in the case of (4), and in which the carbonyl oxygen atom of (3), (4) or (5), or one or both carbonyl oxygen atoms of (6) may be replaced by sulphur; $R_4$ is hydrogen, an aryl radical, or an alkyl radical of 1 to 6 carbon atoms;
L is a halogenated alkyl or alkenyl radical; an alkyl radical (having 1 to 4 carbon atoms) or aryl radical substituted with a vinylsulphonyl group, vinylsulphonamido group or precursors thereof; or a heterocyclic radical containing 1 to 4 halogen atoms attached to carbon atoms adjacent to a nitrogen atom of the ring, the ring being linked directly to K or through an alkylene group having 1 to 4 carbon atoms;
n is 1 to 3.

27 Claims, No Drawings

FIBER-REACTIVE PHOSPHORUS MOTHPROOFING AGENTS

This invention relates to novel organophosphorus esters, to processes for their preparation and to methods for their use in the control of keratin-eating insects.

It is well known that many organophosphorus esters which are available commercially, exhibit high insecticidal activity against such members of the Lepidoptera and Coleoptera families as *Tineola bisselliella* (common clothes moths), *Tinea pellionella* (case-bearing clothes moths) and *Anthrenus verbasci* (carpet beetle). However, when organophosphorus insecticides of this type are applied to keratin, particularly keratinous fibres such as wool, their effectiveness deteriorates during washing, dry cleaning, or exposure to light or heat. (L. L. McDonald, H. P. Boles, and R. E. Bry. Marketing Research Report No. 887, U.S. Department of Agriculture, Washing, 1971; J. H. Lang, R. E. Bry, and L. L. McDonald. Marketing Research Report No. 887-2. Department of Agriculture, Washing, 1971; R. M. Hoskinson and I. M. Russell, J. Text. Inst., 64, 412–418, 1973).

In order to improve the durability of insecticides on wool it has been thought to be desirable to attach them to the wool by covalent bonds. (Farbwerke Hoechst A. G. British Pat. No. 733,471, 13 July, 1955; R. M. Hoskinson and I. M. Russell, J. Text. Inst., 64, 144–152, 1973). Such an approach in the field of dye chemistry has led to the development of dyes which possess excellent durability. (P. Rosenthal, Rev. Prog. Coloration, 7, 23–24, 1976). However, in many instances we have found that when fibre-reactive radicals, of the sort typically used in dye chemistry, are incorporated into an organophosphorus insecticide, the insecticidal properties of the compound are substantially reduced, particularly when it is applied to keratinous material, such as wool, under conditions that favour chemical reaction of the potential insecticide with the keratin. For example, when the compound 0,0-diethyl-0-(4-vinylsulphonyl-phenyl)phosphorothioate is applied to wool by padding from an ethanolic solution, 0.05% on the weight of wool is required to control the feeding damage of *Tineola bisselliella*, but when this compound is applied at 0.2% on the weight of wool by exhaustion from a long aqueous liquor at 100° C. for 60 minutes the treatment is found to be ineffective. Surprisingly, therefore, we have found that when fibre-reactive groups are attached to the organophosphorus esters by a linkage containing: an oxygen or sulphur carbonyl function, such as an ester, amide, urethane, urea, acylurethane, acylurea or their sulphur analogues such as thioester, thioamide, thiourea, acylthiourethane or acylthiourea; or an ether function, where the oxygen is attached to a carbon atom adjacent to the nitrogen atom in a fibre-reactive heteroaromatic group, the novel fibre-reactive compounds possess a high level of insecticidal activity even when applied to keratin under conditions which favour covalent bonding of the compounds to keratin.

Accordingly, there are provided organophosphorus acid esters of the type

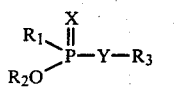 (1)

where $R_1$, $R_2$ and $R_3$ are organic radicals as defined below and X and Y are independently either oxygen or sulphur atoms that is,
(i) where X is oxygen, Y is sulphur; or
(ii) where X is oxygen, Y is oxygen; or
(iii) where X is sulphur, Y is sulphur; or
(iv) where X is sulphur, Y is oxygen.

$R_1$ is an alkyl, alkoxy, alkylamino, dialkylamino or alkylmercapto radical with 1–6 carbon atoms or an aryl or amino radical.

$R_2$ is an alkyl radical with 1–6 carbon atoms.

$R_3$ is a radical of the type

 (2)

where J is a polyvalent aliphatic radical or a polyvalent radical containing an aromatic or heterocyclic ring system; n is an integer from 1 to 3, preferably 1.

K is one of the following groups:

 (3)

 (4)

 (5)

 (6)

—O— (7)

which is attached to J through its oxygen atom in the case of (3) (5) or (6) and through the nitrogen atom in the case of (4), and in which the carbonyl oxygen atom of (3) (4) or (5) or one or both carbonyl oxygen atoms of (6) may be replaced by sulphur; $R_4$ is hydrogen, an aryl radical, or an alkyl radical of 1 to 6 carbon atoms.

L is one of the following organic radicals: a halogenated alkyl radical; a halogenated alkenyl radical, a substituted alkyl radical of 1 to 4 carbon atoms or substituted aryl radical where the preferred substituents are a vinylsulphonyl group, vinylsulphonamide group, or groups capable of forming vinylsulphonyl or vinylsulphonamido groups; or a heterocyclic radical containing 1 to 4 halogen atoms which are attached to carbon atoms adjacent to a nitrogen atom in the heterocyclic ring. Such heterocyclic radicals may be linked directly to K via the heterocyclic ring or may be linked to K through an alkylene group of 1 to 4 carbon atoms.

Typically, such heterocyclic radicals are s-triazinyl, pyrimidinyl, pyridazinyl, pyrazinyl, thiazoyl, benzothiazolyl, quinazolinyl, phthalazinyl and quinoxalinyl radicals substituted with 1 to 4 active halogen atoms, preferably the halogen is chlorine but may be fluorine or bromine. Other substituents may also be present in the heterocyclic radical, such as hydrogen, cyano, alkyl, alkoxy, aryl, aryloxy, trifluoromethyl, amino, alkylamino, dialkylamino, arylamino, hydroxy, sulphonic acid, nitro, alkylsulphonyl, arylsulphonyl or quaternary nitrogen atoms. The nitrogen atom of the quaternary group may be formed typically as part of the pyridine, saturated N-substituted heterocycle or other tertiary amine.

Preferably $R_1$ is an alkoxy of alkylmercapto radical of 2 to 4 carbon atoms, and most preferably is an ethoxy or n-propylmercapto radical.

$R_2$ is preferably a straight chain alkyl radical of 1 to 3 carbon atoms, and is most preferably ethyl.

Preferably X is a sulphur atom and Y is an oxygen atom.

The polyvalent radical J may be a straight chain or branched aliphatic radical of 1 to 10 carbon atoms. Such aliphatic radicals may be saturated or unsaturated and preferably contain other functional groups. Typically, such functional groups may be fluoro, chloro, bromo, cyano, keto, nitro, ester, oxy, thio, amido, lower alkylmercapto, cyanoalkylmercapto, lower alkoxy and the like.

Preferably J is a divalent radical containing an aromatic or heterocyclic ring system. Such an aromatic or heterocyclic ring system is preferably linked directly to Y and may be linked directly to K, or linked to K through a substituent attached to the aromatic or heterocyclic ring. Examples of such substituents are: alkyl such as methyl, ethyl, propyl; alkylmercapto such as ethylmercapto; alkylamino such as ethylamino; dialkylamino such as ethylmethylamino, diethylamino; alkoxy such as ethoxy, propoxy; iminoalkyl such as iminomethyl; alkyloxyiminoalkyl such as ethoxyiminomethyl, and the like.

Other substituents may also be present in the aromatic or heterocyclic ring system. For example, such substituents may be: halo such as fluoro, chloro or bromo; cyano; keto; nitro; lower alkylmercapto; cyanoalkylmercapto; lower alkoxy; lower alkyl; or substituted alkyl, where suitable substituents may be halo, cyano, alkylmercapto, alkoxy or nitro groups.

Examples of suitable aromatic or heterocyclic rings contained in the polyvalent radical J are: phenyl, naphthyl, pyridyl, pyridazinyl, pyrimidinyl, pyrazinyl, pyrazolyl, imidazolyl, 1,2,4-triazolyl 1,3,4-thiodiazolyl, indazolyl, phthalazinyl, quinoxalinyl, cinnolinyl or isoxazolyl ring, and the like; most preferably the ring is phenyl.

K is preferably a carboxylic ester (3), amide (4), ether (7), acylurethane (6) or acylthiourethane (6) group, and most preferably is an ester group (3) which is linked to J through its oxygen atom, or an ether group (7). It is to be appreciated that certain combinations of $R_1$, $R_2$, X, Y, J, K and L give rise to compounds that are more effective than others, particularly certain combinations of K and L. Accordingly, when K is a carboxylic ester (3), amide (4), urethane (5), acylurethane (6) or acylthiourethane (6) group, typical examples of the preferred organic radical L are:

halomethyl, 1-halovinyl or 1,2-dihaloethyl where the preferred halogen is chlorine or bromine;

vinylsulphonylethyl or groups capable of forming vinylsulphonylethyl, such as 2-haloethylsulphonylethyl, and the like; 2-(1,6-dihydro-4,5-dichloro-3-oxo-pyridazin-1-yl) ethyl; 3,6-dichloropyridazin-4-yl;

2,4-dichloropyrimidin-5-yl; 1,4-dichlorophthalazin-6-yl; 2,3-dichloroquinoxalin-6-yl.

Where K is an ether group (7) the preferred radical L is a heteroaromatic radical containing 1 to 4 of any of the following groups: halo such as fluoro, chloro, bromo; alkylsulphonyl such as methyl sulphonyl, ethylsulphonyl. These groups are attached to a carbon atom adjacent to the nitrogen atom in the heteroaromatic ring. Other substituents may also be present such as, halo, amino, alkylamino, dialkylamino, arylamino, nitro, cyano, alkylsulphonyl and the like. Examples of the most preferred organic radical L when K is an ether group (7) are:

4,6-dichloro-s-triazin-2-yl;
4-chloro-6-diethylamino-s-triazin-2-yl;
4-chloro-6-dimethylamino-s-triazin-2-yl;
4-chloro-6-anilino-s-triazin-2-yl;
4-chloro-6-ethylamino-s-triazin-2-yl;
5-chloro-2,6-difluoropyrimidin-4-yl;
2,5,6-trichloropyrimidin-4-yl;
5,6-dichloro-2-methylsulphonylpyrimidin-4-yl;
6-chloro-2-methylsulphonylpyrimidin-4-yl.

The present invention provides processes for the preparation of compounds of the general formula (1). Accordingly a hydroxy or amino compound of the general formula $$(HZ)_n\text{-J-YH} \qquad (11)$$

is reacted in a one- or two-step sequence with an organophosphorus ester halide of the general formula

 (12)

and a compound containing the radical L represented by one of the following general formulae:

 (13)
 (14)
L—N=C=X (15)
L—hal (16)
L—SO$_2$—R$_5$ (17)

where J, L, X, Y, n, $R_1$ and $R_2$ have the above meanings: Z is an oxygen atom or a substituted nitrogen atom where the substituent is $R_4$ and has the above meaning, $R_5$ is an alkyl radical of 1 to 6 carbon atoms and hal is a halogen atom, preferably a chlorine atom.

Compounds of the general formulae (11), (12), (13), (14), (15), (16) and (17), which are used as starting materials are described in the literature or can be prepared according to conventional processes.

To effect the preparation of compounds of the general formula (1) a compound of formula (11) may be reacted simultaneously with a compound of formula (12) and a compound of formulae (13), (14), (15), (16), or (17). Or the compounds of formula (1) may be prepared by a two-step reaction sequence whereby a compound of formula (11) is reacted initially with a compound of formula (12) and the product from this reaction reacted with a compound of formula (13), (14), (15), (16), or (17). Alternatively, a compound of formula (11) is reacted initially with a compound of the formulae (13), (14), (15), (16), or (17), and the product from this reaction is reacted with a compound of the formula (12).

Preferably the reactions are carried out in a two-step sequence whereby a compound of formula (11) is phosphorylated by a compound of the formula (12) and the resulting product, which may be isolated, is reacted with a compound of the formula (13), (14), (15), (16), or (17).

Optionally these reactions are carried out in the presence of a solvent or diluent and reactions involving compounds of the formula (12), (13), (16) and (17) are optionally carried out in the presence of an acid acceptor.

The reactions for the preparation of the new compounds of the formula (1) are preferably carried out with conjoint use of a suitable solvent or diluent. Practically all inert organic solvents can be used for this purpose, especially aromatic and aliphatic, optionally chlorinated, hydrocarbons such as benzene, toluene, xylene, methylenechloride, chloroform, carbon tetrachloride and chlorobenzene; ethers, for example, diethyl ether, dibutylether or dioxane; ketones such as acetone methylethylketone, methylisopropylketone, and methylisobutyl ketone; nitriles, for example, acetonitrile and propionitrile; and amides such as dimethylformamide and dimethylacetamide.

All customary acid-bonding agents can be used as acid acceptors. The following have proved particularly suitable; alkali metals, alkali metal carbonates and alkali metal alcoholates, such as sodium and potassium, sodium and potassium carbonate, methylate, ethylate, tert-butylate, and also aliphatic, aromatic and heterocyclic amines, for example, triethylamine dimethylaniline, dimethylbenzylamine, pyridine, collidine. Also particularly suitable acid-binding agents are polymeric cationic resins, such as those manufactured by Rohm and Haas and marketed under the name of Amberlyst resins.

The reaction temperatures can be varied within a fairly wide range but when a two-step reaction sequence is used it is preferable to use as low a temperature as practicable in the first reaction step to avoid undesirable side-reactions. In general, the reactions are carried out between $-30°$ C. and $+100°$ C.

The reactions are in general allowed to take place under normal pressure. To carry out the process, the starting materials are generally employed in equimolar amounts. The reactions are generally carried out in a suitable solvent, and, where necessary, in the presence of an acid-acceptor. The reaction mixture is thereafter stirred for several hours. If the preparation of compounds of the formula (1) are carried out in a two-step reaction sequence, it may be desirable to isolate the intermediate product in accordance with customary methods; but preferably the intermediate product is reacted without isolation in the second-step of the reaction sequence in the same reaction medium.

The new compounds are generally obtained either as crystalline solids or in the form of oils which in most cases cannot be distilled without decomposition, but can be freed from the last volatile constituents by so-called "slight distillation"—that is to say by prolonged heating under reduced pressure to moderately elevated temperatures, and can be purified in this way. They are characterised by their melting points or nuclear magnetic resonance spectra.

It is to be appreciated that the compounds may be prepared by alternative routes to those discussed above. For example, some compounds of the formula (1) may be prepared by the following reaction sequence:

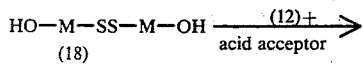

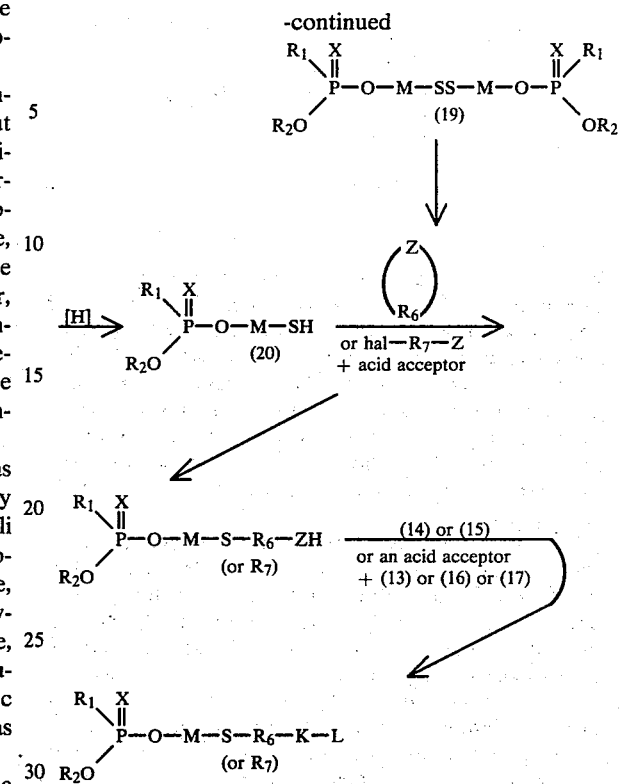

where $R_1$, $R_2$, X, Z, K, L and hal have the above meaning; M is a divalent aromatic or heteroaromatic radical; $R_6$ is an ethylene radical or a divalent alkylethylene radical of 3 to 10 carbon atoms and $R_7$ is an alkylene radical of 2 to 10 carbon atoms. Suitable reducing agents for the reduction of the disulphides of the formula (19) to the thiols of the formula (20) are well known to those skilled in the art and may include aromatic or aliphatic phosphines, such as triphenylphosphines or tributylphosphines; metal hydrides, such as sodium borohydride, and lithium aluminium hydride; metals in the presence of acids, such as zinc, tin or iron in the presence of acetic acid or hydrochloric acid and the like; amphoteric metals in the presence of a base, such as zinc and alcoholic potassium hydroxide; metal sulphides such as sodium sulphide; organic thiols, and the like.

The alkylation of the thiol (20) may be carried out in any of the inert solvents listed above but is preferably carried out in an alcoholic solvent, such as methanol or ethanol in the presence of a base. Suitable alkylating agents may be halo alcohols, such as 2-chloroethanol, 2-bromoethanol, 3-chloropropanol, 3-chloro-2-propanol and the like but, preferably are ethylene oxide or alkyl-1,2-epoxides such as propylene oxide 1,2-butylene oxide, 1,2-cyclohexane oxide, styrene oxide and the like.

Other alternative routes for the preparation of compounds of formula (1) may also be envisaged. For example, compounds of the type:

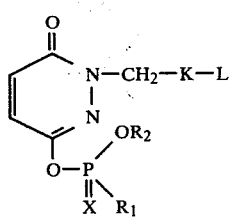

where K, L, $R_1$ $R_2$ have the above meaning, may be prepared by phosphorylating maleic hydrazide with compounds of the formula (12) and reacting the product with formaldehyde as described by S. Du Breuil J. Org. Chem., 26, 3382-6, (1961). This hydroxy organophosphate may then be reacted with compounds of the formula (13), (14) or (15) in the manner described above to yield compounds of the formula (1). Such alternative processes are considered to be within the scope of the present invention.

As has already been mentioned, organophosphorus esters according to the invention, are distinguished by good insecticidal activity and may be employed successfully in controlling the feeding damage of keratin-digesting insects, especially on wool textiles. Examples of such keratin digesting insects are: Tineola bisselliella, Tineola furciferella, Tinea pellionella, Tinea columbariella, Trichophage tapetzella, Trichophage perena, Accedes pallescentella, Attagenus piceus, Attagenus pellio, Anthrenus verbasci, Anthrenus vorax, Anthrenus pimpinella, Anthrenus scrophulariae, and Anthrenocerus australis.

The present invention also provides a process for the treatment of keratinous material with compounds (1) according to the invention.

For the purpose of this invention the keratin is preferably in the fibrous form such as the fibres from sheep, or other animals but it may also be in the form of feathers, hides, animal horns or products made from them.

The keratinous fibres may still be attached to the animal skins or may be in the form of loose fibers, sliver, yarn, fabric, garments, carpet, or in any other form that may be conveniently treated.

The fibrous material is preferably wool, but this may be wholly or partially replaced by one or more other animal fibres or partially replaced by one or more non-keratinous fibres such as cotton, regenerated cellulose, cellulose acetate, polyester, polyamide, polyolefin, polyvinylhalide and the like.

Accordingly, from 0.005 to 3% by weight, preferably from 0.01 to 1% of the compound (1) of the invention is applied to keratinous material by either of the following methods.

(a) By treatment with a solution of the compound in an organic solvent. Suitable organic solvents include perchloroethylene, trichloroethylene, white spirit, ethanol, benzene or other hydrocarbons or halogenated hydrocarbons and the like.

(b) By treatment with an emulsion or dispersion of the compound or with an emulsion or dispersion of a solution in a water-immiscible or a water-miscible solvent in water. Such emulsions or dispersions preferably contain surface active agents. Subsequently, the material is dried to remove water and solvent if present. Chemical reaction between the compound (1) and keratin may be induced to occur during the treatment, or in a subsequent curing operation, for example, by heating. Heating may be effected by contacting the treated fibrous material with a heated fluid, e.g., hot air, steam, boiling water, a heated object, or by radiative means.

The application of the fibrous material may be by padding, spraying, brushing, dipping or the like, or preferably by an exhaustion technique from a long liquor.

During such application the fibrous materials of compounds of the present invention, various agents to modify other textile properties may also be added. It is to be appreciated that the presence of such agents may be used to enhance the evenness of application and degree of durability of compounds of the invention. Examples of these agents are well known to those skilled in the art of textiles.

It is also to be appreciated that the performance of compounds according to the invention may be varied by the mode of its application to the keratin. For example application from organic solvents by padding, and the like generally results in lower application levels being required to control keratin-digesting insects, but this mode of application does not produce a treatment which is as durable as that obtained when the compounds are applied from aqueous solutions or emulsions by exhaustion from a long liquor.

The processes of the present invention have been found to have, in many cases, advantages over prior art mothproofing of wool and this is illustrated in the examples.

The following examples are provided to illustrate the present invention but are not to be construed as limiting the invention in any way.

The process of the present invention is illustrated by the following preparative examples.

EXAMPLE 1

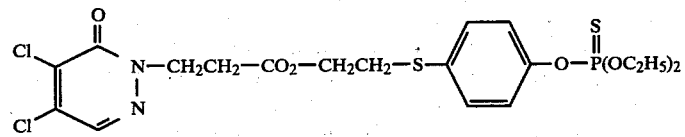

A solution of 9.5 g of diethylphosphorothiochloridate (0.05 moles) in 30 mls of anhydrous toluene were added dropwise over 30 minutes to a stirred solution of 9.6 g of the sodio salt of 4-(2-hydroxyethylthio)phenol (0.05 moles) in 25 mls of anhydrous dimethylformamide at 0° C. The mixture was slowly warmed to 20° C. over a period of 2 hours and after stirring for a further 8 hours at 20° C. the mixture was poured into 400 mls. of water. The organic layer was separated and the aqueous layer extracted with 100 mls of toluene. The combined organic layers were washed with 100 mls×2 of 10% sodium hydroxide solution, dried over sodium sulphate and the solvent removed under reduced pressure to yield 13.2 g of 0,0-diethyl-0-4(2-hydroxyethylthio(-phenylphosphorothioate as a pale yellow oil.

To a solution of 12.9 g 0,0-Diethyl-0-(4-(2-hydroxyethylthio)phenyl)phosphorothioate (0.04 moles) in 20 mls of anhydrous toluene was added a solution of 10.2 g of 3-(1,6-dihydro-6-oxo-4,5-dichloropyridazin-1-yl)propionylchloride (0.04 moles) in 10 mls of anhydrous toluene and 4.84 g of collidine (0.04 moles). The resulting mixture was stirred at room temperature for 3 hours, filtered and the solvent removed under reduced pressure to yield 21 g of 0,0-diethyl-0-(4-(2-(3-(1,6-dihydro-6-oxo-4,5-dichloropyridazin-1-yl)propionyloxy)ethylthio)phenyl)phosphorothioate.

EXAMPLE 2

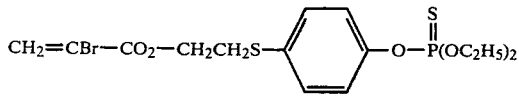

A solution of 9.4 g of diethylphosphorothiochloridate diethylphosphorochloridothioate (0.05 moles) in 30 ml of toluene was added dropwise over 30 min to a stirred solution of 9.6 g of the sodio salt of 4-(2-hydroxyethylthio)phenyl (0.05 moles) in 25 ml of anhydrous dimethylformamide at 0° C. The temperature was then raised to 20° C. over 2 hours and the mixture stirred for a further 8 hours. 12.5 g of 2,3-dibromopropionylchloride (0.05 moles) and 12.1 g of collidine (0.1 moles) was added. After a further 2 hours the mixture was poured into 500 mls of water and the organic layer separated. The aqueous layer was extracted with 100 mls of toluene and the combined organic layers washed successively with 100 mls × 2 of 10% hydrochloric acid and 100 mls × 2 of 10% sodium hydroxide, dried over anhydrous sodium sulphate and the solvent removed under vacuum to leave 18.7 g of a pale yellow oil.

EXAMPLE 3

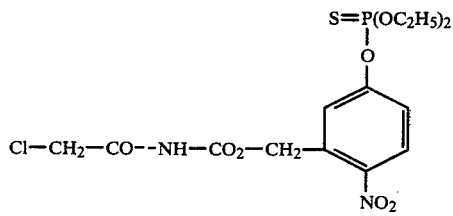

To a solution of 8.45 g of 3-hydroxymethyl-4-nitrophenol (0.05 mole) and 9.5 g of 0,0-diethylphosphorothiochloridate (0.05 mole) in 70 ml of dry ethylmethyl ketone was added 9.66 of anhydrous potassium carbonate (0.07 mole). The mixture was heated under reflux for one hour, filtered and the solvent removed under reduced pressure. The residue was dissolved in 50 ml of chloroform, washed successively with 2×30 ml of 10% sodium hydroxide and 2×30 ml of water, dried over anhydrous sodium sulphate and the chloroform removed under reduced pressure to yield 15.2 g of 0,0-diethyl-0-(4-nitro-3-hydroxymethylphenyl)phosphorothioate as a pale yellow oil.

To a solution of 12.84 g of 0,0-diethyl-0-(4-nitro-3-hydroxymethylphenyl)phosphorothioate (0.04 mole) in 50 mls of anhydrous benzene was added with stirring 4.75 g of chloroacetylisocyanate (0.04 mole). The solution was stirred at room temperature overnight and the solvent removed under reduced pressure to yield 12.4 g of 0,0-diethyl-0-(4-nitro-3-(N-(chloroacetyl)carbamoyloxymethyl)phenyl)phosphorothioate.

EXAMPLE 4

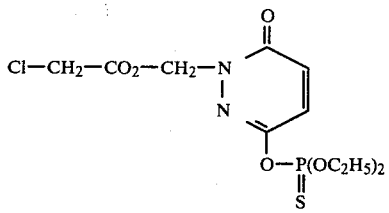

To a solution of 8.8 g of 0,0-diethyl-o-(1,6-dihydro-6-oxo-1-hydroxymethylpyridazin-3-yl)phosphorothioate (0.03 moles) in 30 ml of anhydrous toluene was added 3.5 g of chloroacetyl chloride (0.03 moles) and 3.7 g collidine (0.03 moles). The mixture was stirred at room temperature for 4 hours, filtered, and the solvent removed under reduced pressure to yield 10.5 g of 0,0-diethyl-0-(1,6-dihydro-6-oxo-1-chloroacetyloxymethylpyridazin-3-yl)phosphorothioate as a colourless oil.

EXAMPLE 5

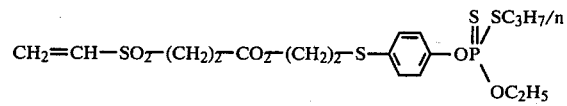

To a solution of 12.5 g of 4,4'-dihydroxydiphenyldisulphide (0.05 mole) and 21.8 g of 0-ethyl-S-n-propylphosphorodithiochloridate (0.1 mole) in 70 ml of anhydrous acetonitrile was added 17.2 g of anhydrous potassium carbonate (0.13 mole). The mixture was heated under reflux for 2 hours, filtered and the solvent removed under reduced pressure. The residue was dissolved in 80 ml of di ethylether, washed successively with 2×30 ml of 10% aqueous sodium hydroxide and 30 ml of water, diluted with 40 ml of methanol and 10 ml of water, purged with nitrogen and treated with 14.1 g of tributylphosphine (0.07 mole). After 1 hour the solution was extracted with 3×50 ml of 10% aqueous sodium hydroxide. The aqueous layer was washed with 3×30 ml of 20% of di ethylether in hexane, acidified to pH 2 with dilute hydrochloric acid and then extracted with 3×50 ml of di ethylether. The di ethylether was removed under reduced pressure, the residue dissolved in 100 ml of ethanol containing 0.01 g of sodium hydroxide and 4.4 g of ethylene oxide (0.10 mole) in 50 ml ethanol was added at 0° C. over 30 min. After 1 hour the solvent was removed under reduced pressure, the residue dissolved in 100 ml of anhydrous toluene, 12.1 g collidine (0.1 mole) and 18.2 g of 3-(vinylsulphonyl)propionylchloride (0.1 mole) added and the mixture stirred at room temperature overnight. The mixture was washed successively with 40 ml of water, 3×30 ml of dilute hydrochloric acid, 3×30 ml 10% aqueous sodium carbonate, dried with magnesium sulphate and the solvent removed under reduced pressure to yield 40 g of a pale yellow oil.

The compounds listed in Table 1 below could be obtained by methods analogous to those described above.

4,303,652

TABLE 1

| EXAMPLE NO. | Structure |
|---|---|
| 6 | $Cl-CH_2-CO_2-CH_2CH_2-S-\langle C_6H_4\rangle-O-\overset{S}{\overset{\|}{P}}(OC_2H_5)_2$ |
| 7 | $CH_2=CCl-CO_2-CH_2CH_2-S-\langle C_6H_4\rangle-O-\overset{S}{\overset{\|}{P}}(OC_2H_5)_2$ |
| 8 | $CH_2Cl-CHCl-CO_2-CH_2CH_2-S-\langle C_6H_4\rangle-O-\overset{S}{\overset{\|}{P}}(OC_2H_5)_2$ |
| 9 | $Cl-CH_2CH_2-SO_2-CH_2CH_2-CO_2-CH_2CH_2-S-\langle C_6H_4\rangle-O-\overset{S}{\overset{\|}{P}}(OC_2H_5)_2$ |
| 10 | $CH_2=CH-SO_2-CH_2CH_2-CO_2-CH_2CH_2-S-\langle C_6H_4\rangle-O-\overset{S}{\overset{\|}{P}}(OC_2H_5)_2$ |
| 11 | $Cl-CH_2-CO-NH-CO_2-CH_2CH_2-S-\langle C_6H_4\rangle-O-\overset{S}{\overset{\|}{P}}(OC_2H_5)_2$ |
| 12 | $CH_2Br-CHBr-CO-NH-CO_2-CH_2CH_2-S-\langle C_6H_4\rangle-O-\overset{S}{\overset{\|}{P}}(OC_2H_5)_2$ |
| 13 | $CH_2Cl-CHCl-CO_2-CH_2CH_2-S-\langle C_6H_3(Cl)\rangle-O-\overset{S}{\overset{\|}{P}}(OC_2H_5)_2$ |
| 14 | $CH_2Cl-CHCl-CO_2-CH_2CH_2S-\langle C_6H_3(Cl)\rangle-O-\overset{S}{\overset{\|}{P}}(OC_2H_5)_2$ |
| 15 | $CH_2=CBr-CO_2-CH_2CH_2-S-\langle C_6H_4\rangle-O-\overset{S}{\overset{\|}{P}}(SC_3H_7/n)(OC_2H_5)$ |
| 16 | $CH_2Br-CHBr-CO_2-CH_2CH_2-S-\langle C_6H_4\rangle-O-\overset{S}{\overset{\|}{P}}(SC_3H_7/n)(OC_2H_5)$ |
| 17 | $Cl-CH_2CH_2-SO_2-CH_2CH_2-CO_2-CH_2CH_2-S-\langle C_6H_4\rangle-O-\overset{S}{\overset{\|}{P}}(SC_3H_7/n)(OC_2H_5)$ |
| 18 | $Cl-CH_2-CO-NH-CO_2-CH_2CH_2-S-\langle C_6H_4\rangle-O-\overset{S}{\overset{\|}{P}}(SC_3H_7/n)(OC_2H_5)$ |
| 19 | $CH_2=CBr-CO_2-CH_2CH_2-N-N=C(SCH_3)-N=C-O-\overset{S}{\overset{\|}{P}}(OC_2H_5)_2$ |
| 20 | $Cl-CH_2CH_2-SO_2-CH_2CH_2-CO_2-CH_2CH_2-N-N=C(SCH_3)-N=C-O-\overset{S}{\overset{\|}{P}}(OC_2H_5)_2$ |

TABLE 1-continued
EXAMPLE NO.
21 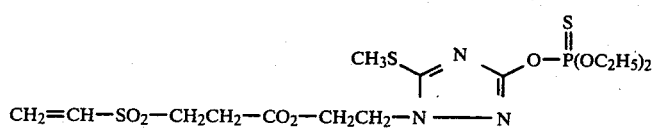
22 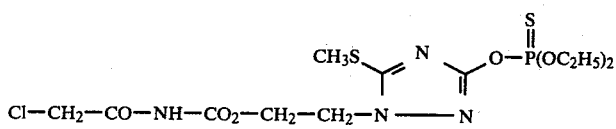
23 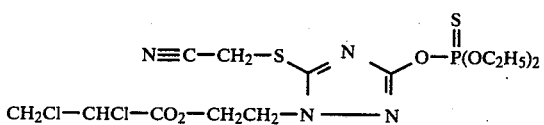
24 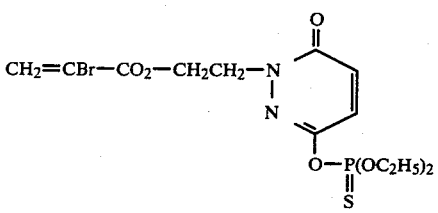
25 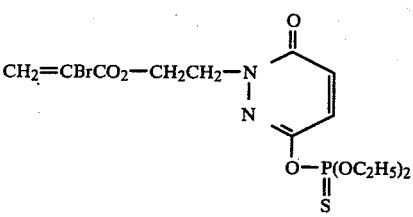
26 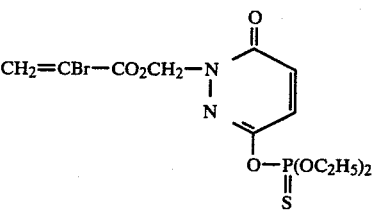
27 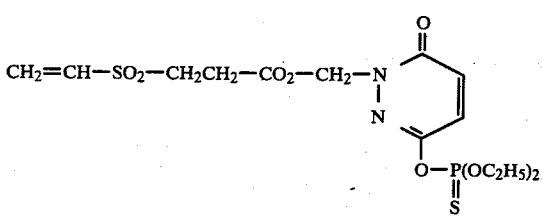
28 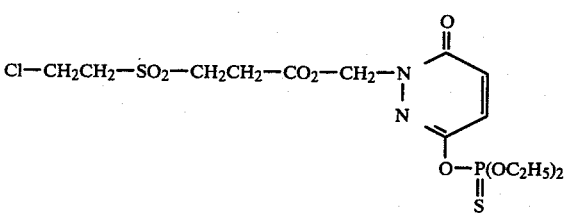
29 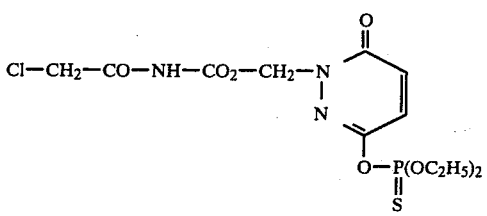

TABLE 1-continued

| EXAMPLE NO. | Structure |
|---|---|
| 30 | Cl—CH$_2$—CO—NH—CO$_2$CH$_2$—N(pyridazinone ring with O—P(=S)(SC$_3$H$_7$/n)(OC$_2$H$_5$)) |
| 31 | Cl—CH$_2$—CO$_2$—CH$_2$CH$_2$—S—(pyridazine N=N)—O—P(=S)(OC$_2$H$_5$)$_2$ |
| 32 | CH=CBr—CO$_2$—CH$_2$CH$_2$—S—(pyridazine N=N)—O—P(=S)(OC$_2$H$_5$)$_2$ |
| 33 | Cl—CH$_2$CH$_2$—SO$_2$—CH$_2$CH$_2$—CO$_2$—CH$_2$CH$_2$—S—(pyridazine N=N)—O—P(=S)(OC$_2$H$_5$)$_2$ |
| 34 | Cl—CH$_2$—CO—NH—CO$_2$—CH$_2$CH$_2$—S—(pyridazine N=N)—O—P(=S)(OC$_2$H$_5$)$_2$ |
| 35 | CH$_2$=CBr—CO$_2$—CH$_2$CH$_2$—S—(pyridazine N=N)—O—P(=S)(SC$_3$H$_7$/n)(OC$_2$H$_5$) |
| 36 | CH$_2$=CBr—CO$_2$—CH(CH$_3$)CH$_2$—S—(phenyl)—O—P(=S)(SC$_3$H$_7$)(OC$_2$H$_5$) |
| 37 | CH$_2$=CHSO$_2$CH$_2$CH$_2$CO$_2$CH$_2$—(2-NO$_2$-phenyl)—O—P(=S)(OC$_2$H$_5$)$_2$ |
| 38 | ClCH$_2$CH$_2$SO$_2$CH$_2$CH$_2$CO$_2$CH$_2$—(2-NO$_2$-phenyl)—O—P(=S)(OC$_2$H$_5$)$_2$ |
| 39 | ClCH$_2$CO$_2$CH$_2$—(2-NO$_2$-phenyl)—O—P(=S)(OC$_2$H$_5$)$_2$ |
| 40 | CH$_2$=CBrCO$_2$CH$_2$—(2-NO$_2$-phenyl)—O—P(=S)(OC$_2$H$_5$)$_2$ |
| 41 | BrCH$_2$CHBrCONHCO$_2$CH$_2$—(2-NO$_2$-phenyl)—O—P(=S)(OC$_2$H$_5$)$_2$ |

TABLE 1-continued

| EXAMPLE NO. | |
|---|---|
| 42 | ClCH$_2$CONHCO$_2$CH$_2$—⟨C$_6$H$_3$(NO$_2$)⟩—O—P(=S)(OC$_2$H$_5$)$_2$ (NO$_2$ ortho to O-P) |
| 43 | ClCH$_2$CONHCO$_2$CH$_2$—⟨C$_6$H$_3$(NO$_2$)⟩—O—P(=S)(OC$_2$H$_5$)$_2$ |
| 44 | NO$_2$—⟨C$_6$H$_3$(CH$_2$OCONHCOCH$_2$Cl)⟩—O—P(=S)(SC$_3$H$_7$-n)(OC$_2$H$_5$) |
| 45 | NO$_2$—⟨C$_6$H$_3$(CH$_2$OCOCBr=CH$_2$)⟩—O—P(=S)(SC$_3$H$_7$-n)(OC$_2$H$_5$) |
| 46 | NO$_2$—⟨C$_6$H$_3$(CH$_2$OCOCH$_2$CH$_2$SO$_2$CH=CH$_2$)⟩—O—P(=S)(SC$_3$H$_7$-n)(OC$_2$H$_5$) |
| 47 | [2-CH$_3$, 6-(pyrimidinyl) with CH$_2$OCONHCOCH$_2$Cl substituent]—O—P(=S)(OC$_2$H$_5$)$_2$ |
| 48 | [2-CH$_3$, 6-(pyrimidinyl) with C(CH$_3$)$_2$OCONHCOCH$_2$Cl substituent]—O—P(=S)(OC$_2$H$_5$)$_2$ |
| 49 | ClCH$_2$CONHCONH—⟨isoxazolyl⟩—O—P(=S)(OC$_2$H$_5$)$_2$ |
| 50 | ClCH$_2$CONH—⟨isoxazolyl⟩—O—P(=S)(OC$_2$H$_5$)$_2$ |
| 51 | ClCH$_2$CONHCO$_2$CH$_2$CH$_2$N—⟨(CH$_3$)pyrazolyl⟩—O—P(=S)(OC$_2$H$_5$)$_2$ |
| 52 | [Cl, N, (C$_2$H$_5$)$_2$N-triazinyl]—O—CH$_2$CH$_2$S—⟨C$_6$H$_4$⟩—O—P(=S)(SC$_3$H$_7$-n)(OC$_2$H$_5$) |

The following examples demonstrate the insecticidal properties of the compounds of the invention.

Samples of wool fabric weighing 2 g were impregnated with 4 ml of ethanol containing various amounts of the active compounds and dried in a laboratory oven at 60° C. The minimum concentration of active compound on the weight of wool required to control the feeding damage of keratin-digesting insects was determined essentially as described in AATCC test method 24-1974. The results can be seen from Table 2 below.

TABLE 2

| Active Compound (as in example) | Minimum concentration (% wt. on wt. of wool) required to control: | |
|---|---|---|
| | Tineola bisselliella | Anthrenus verbasci |
| 1 | 0.07 | 0.05 |
| 2 | 0.06 | 0.04 |
| 3 | 0.005 | 0.005 |
| 4 | 0.005 | 0.005 |
| 5 | 0.03 | 0.03 |
| 6 | 0.04 | 0.02 |
| 7 | 0.07 | 0.05 |
| 8 | 0.07 | 0.05 |
| 9 | 0.07 | 0.04 |
| 10 | 0.07 | 0.04 |
| 11 | 0.05 | 0.02 |
| 12 | 0.04 | 0.04 |
| 13 | 0.03 | 0.04 |
| 14 | 0.07 | 0.04 |
| 15 | 0.04 | 0.03 |
| 16 | 0.03 | 0.05 |
| 17 | 0.04 | 0.04 |
| 18 | 0.01 | 0.01 |
| 19 | 0.07 | 0.03 |
| 20 | 0.006 | 0.03 |
| 21 | 0.005 | 0.03 |
| 22 | 0.005 | 0.03 |
| 23 | 0.03 | 0.06 |
| 24 | 0.04 | 0.03 |
| 25 | 0.05 | 0.07 |
| 26 | 0.006 | 0.005 |
| 27 | 0.005 | 0.005 |
| 28 | 0.005 | 0.005 |
| 29 | 0.02 | 0.007 |
| 30 | 0.01 | 0.01 |
| 31 | 0.01 | 0.02 |
| 32 | 0.01 | 0.01 |
| 33 | 0.005 | 0.005 |
| 34 | 0.005 | 0.02 |
| 35 | 0.07 | 0.03 |
| 36 | 0.03 | 0.03 |
| 37 | 0.1 | 0.05 |
| 38 | 0.2 | 0.1 |
| 39 | 0.07 | 0.05 |
| 40 | 0.15 | 0.1 |
| 41 | 0.07 | 0.05 |
| 42 | 0.03 | 0.05 |
| 43 | — | 0.2 |
| 44 | 0.005 | 0.005 |
| 45 | 0.1 | 0.08 |
| 46 | 0.06 | 0.05 |
| 47 | 0.03 | 0.05 |
| 48 | 0.03 | 0.05 |
| 49 | 0.03 | 0.03 |
| 50 | 0.05 | 0.03 |
| 51 | 0.05 | 0.03 |
| 52 | 0.03 | 0.03 |

The following examples demonstrate the excellent durability of the compounds according to the invention.

To produce a suitable aqueous emulsion of the active compound a 10% emulsifiable concentrate was prepared by mixing 0.03 g of the active compound with 0.24 g of xylene containing 0.03 g of an alkylarylpolyglycolether and this concentrate was diluted with 600 mls of water containing 1.2 g of ammonium sulphate and 1 g of acetic acid.

30 g of wool was treated with this emulsion in a laboratory dyeing apparatus by circulating the liquor while the temperature was raised to between 98° C. and 100° C. over 30 minutes and held at this temperature for a further 30 minutes. The spent liquor was then removed and the wool rinsed with 600 mls of cold water and dried.

Samples of the treated fabric were either exposed to sunlight, hand washed, or drycleaned before being biologically tested for insectproofness essentially as described in AATCC test method 24-1974.

The degree of exposure to sunlight was assessed by comparing the fading of a standard set of blue dyes on a scale of 1-8 as described by British Standards Institute in BS 1006:1961. 1 means poor sunlight stability, 8 means good sunlight stability.

The following Table 3 shows the degree of sunlight exposure, number of washes and number of drycleans required to induce the samples to fail the biological test. Examples, A, B, C, D are known organophosphate insecticides and are given by way of comparison.

TABLE 3

| Active Compound (as in example) | Sunlight exposure index | Number of hand washes | Number of drycleans |
|---|---|---|---|
| A $CH_3S-\bigcirc-O-\overset{S}{\underset{\|}{P}}(OCH_3)_2$ with $CH_3$ | 5 | 5 | 2 |
| B (diazinon-like structure with $O-P(OC_2H_5)_2$, $S$) | 1–2 | 1 | 1 |
| C $(C_2H_5)_2N-\underset{N}{\overset{N}{\bigcirc}}-O-\overset{S}{\underset{\|}{P}}(OC_2H_5)_2$ with $CH_3$ | 1–2 | 1 | 1 |
| D $O_2N-\bigcirc-O-\overset{S}{\underset{\|}{P}}(OC_2H_5)_2$ | 1–2 | 1 | 1 |
| 2 | >7 | >10 | >10 |
| 5 | ≧8 | >10 | >10 |
| 6 | >7 | >10 | >10 |
| 10 | >7 | >10 | >10 |
| 11 | >7 | 8 | 10 |
| 15 | ≧8 | >10 | >10 |
| 16 | ≧8 | >10 | >10 |
| 19 | >5 | >10 | >10 |
| 21 | >5 | >10 | >10 |
| 26 | >6 | >10 | >10 |
| 27 | >6 | >10 | >10 |
| 32 | >5 | >10 | >10 |
| 33 | >5 | >10 | >10 |
| 52 | >7 | >10 | >10 |

The claims defining the invention are as follows:
1. A compound of the formula:

wherein:
X and Y are independently O or S;
$R_1$ is alkyl, alkoxy, alkylamino, dialkylamino or alkylmercapto having 1 to 6 carbon atoms; amino or phenyl;
$R_2$ is alkyl having 1 to 6 carbon atoms;
$R_3$ is a group of the formula:

$$-J-(K-L)_n \quad (2)$$

wherein:

J is a cyclic group selected from the group consisting of phenyl, naphthyl, pyridyl, pyridazinyl, pyrimidinyl, pyrazinyl, pyrazolyl, imidazolyl, 1,2,4-triazolyl, 1,3,4-thiodizolyl, indazolyl, phthalazinyl, quinoxalinyl, cinnolinyl and isoxazolyl, which cyclic group is linked directly to the group Y and is is linked to the group K by a divalent alkyl group or a divalent alkylmercapto group containing 1 to 4 carbon atoms, said divalent group being linked to the group K through a carbon atom, and said cyclic group being unsubstituted or substituted by substituents selected from the group consisting of halo, cyano, keto, nitro, lower alkylmercapto, cyanoalkylmercapto, lower alkoxy, lower alkyl and lower alkyl substituted with substituents selected from the group consisting of halo, cyano, lower alkylmercapto, lower alkoxy and nitro groups;

K is one of the following groups:

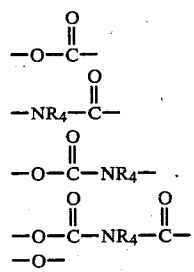

linked to J through the oxygen atom in the case of (3), (5) or (6), and through the nitrogen atom in the case of (4), and in which the carbonyl oxygen atom of (3), (4) or (5), or one or both carbonyl oxygen atoms of (6) may be replaced by sulphur; $R_4$ is hydrogen, an aryl group having 6 to 10 carbon atoms, or an alkyl group of 1 to 6 carbon atoms;

L is a halogenated alkyl or alkenyl group, an alkyl group having 1 to 4 carbon atoms or an aryl group having 6 to 10 carbon atoms substituted with a vinylsulphonyl group, vinylsulphonamido group or a group capable of forming vinylsulphonyl or vinylsulphonylamido groups, or a 6-membered nitrogen heterocyclic group containing 2 to 3 nitrogen atoms and having attached to carbon atoms adjacent to a nitrogen atom of the ring 1 to 4 halogen atoms, and optionally being further substituted by substituents selected from the group consisting of cyano, an alkyl or alkoxy group containing 1 to 4 carbon atoms, an aryl, aryloxy, arylamino or arylsulphonyl group containing 6 to 10 carbon atoms, trifluoromethyl, amino, an alkylamino, dialkylamino or alkylsulphonyl group wherein the alkyl contains 1 to 4 carbon atoms and quaternary ammonium groups; the ring being linked directly to K or through an alkylene group having 1 to 4 carbon atoms;

n is 1 to 3.

2. A mothproofing composition comprising an effective amount of a compound of formula I as defined in claim 1 in an appropriate liquid carrier.

3. A compound as defined in claim 1 wherein the heterocyclic group within the substituent L is selected from the group consisting of s-triazinyl, pyrimidinyl, pyridazinylpyrazinyl, pyrazinyl, thiazolyl, benzothiazolyl, quinazolinyl, phthalazinyl and quinazolinyl.

4. A compound as defined in claim 1 wherein K is the group (7) and L is an aromatic 6-membered nitrogen heterocyclic group containing attached to carbon atoms adjacent to a nitrogen of the ring 1 to 4 substituents selected from the group of 1 to 4 halogen atoms selected from the group consisting of fluorine, chlorine and bromine, and methylsulphonyl and ethylsulphonyl, and optionally being further substituted by substituents selected from the group consisting of halogen, amino, an alkylamino, dialkylamino or alkylsulphonyl group wherein the alkyl contains 1 to 4 carbon atoms, aryl amino containing 6 to 10 carbon atoms, nitro and cyano.

5. A compound as defined in claim 1 wherein L is selected from the group consisting of 4,6-dichloro-s-triazin-2-yl; 4-chloro-6-diethylamino-s-triazin-2-yl; 4-chloro-6-dimethylamino-s-triazin-2-yl; 4-chloro-6-anilino-s-triazin-2-yl; 4-chloro-6-ethylamino-s-triazin-2-yl; 5-chloro-2,6-difluoropyrimidin-4-yl; 2,5,6-trichloropyrimidin-4-yl; 5,6-dichloro-2-methylsulphonylpyrimidin-4-yl; and 6-chloro-2-methylsulphonylpyrimidin-4-yl.

6. A compound as defined in claim 1 wherein:

$R_1$ is alkoxy or alkylmercapto having 2 to 4 carbon atoms;

$R_2$ is a straight chain alkyl group having 1 to 3 carbon atoms;

X is sulphur and Y is oxygen;

J is selected from the group consisting of 4-ethylenethiophenyl, 4-propylenethiophenyl, 3-methylene-4-nitrophenyl, 2-ethylene-3-methylthio-1,2,3-triazol-5-yl, 1,6-dihydro-6-oxo-1-methylenepyridazine-3-yl, 1,6-dihydro-6-oxo-1-ethylenepyridazin-3-yl, 3-ethylenethiopyridazin-6-yl;

K is the group

L is halomethyl, 1-halovinyl, or 1,2-dihaloethyl; vinylsulphonylethyl, a group capable of forming vinylsulphonylethyl; 2-(1,6-dihydro-4,5-dichloro-3-oxo-pyridazin-1-yl)ethyl; 3,6-dichloro-pyridazinyl-4-yl; 2,4-dichloropyrimidin-5-yl; 1,4-dichlorophthalazin-6-yl; or 2,3-dichloroquinoxalin-6-yl;

n is 1.

7. A compound as defined in claim 6 wherein:

$R_1$ is ethoxy or n-propylmercapto;

$R_2$ is ethyl;

J is 4-(2-ethyl(thio)phenyl;

L is vinylsulphonylethyl or a group capable of forming vinylsulphonylethyl.

8. A compound as defined in claim 1 wherein the group capable of forming vinylsulphonyl or vinylsulphonylamido groups is a 2-haloethylsulphonyl or 2-haloethylsulphonylamido group.

9. A compound of the formula:

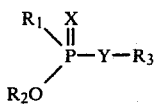

wherein:
R₁ is ethoxy or n-propylmercapto;
R₂ is ethyl;
X is sulphur and Y is oxygen;
R₃ is a radical of the formula:

-J-(K-L)ₙ

J is 4-(2-ethylthio)phenyl;

K is the group -O-CO-,

L is 1-hydrovinyl or 1,2-dihaloethyl wherein halo is bromo or chloro; and
n is 1.

10. A compound of the formula:

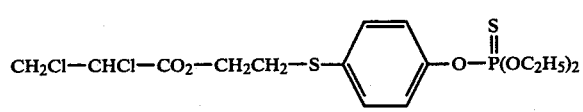

11. A compound of the formula:

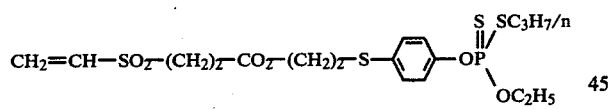

12. A compound of the formula:

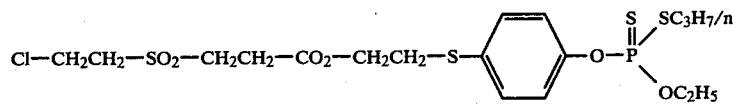

13. A compound of the formula:

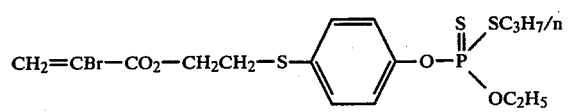

14. A compound of the formula:

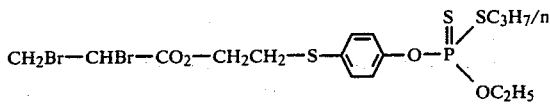

15. A compound of the formula:

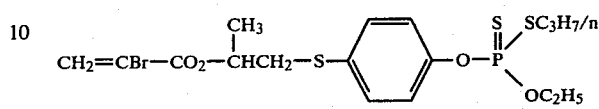

16. A compound of the formula:

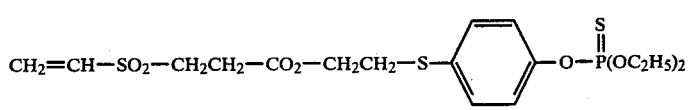

17. A compound of the formula:

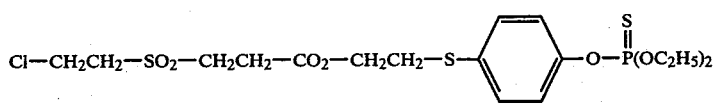

18. A compound of the formula:

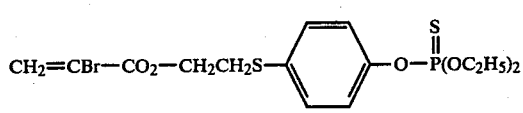

19. A compound of the formula:

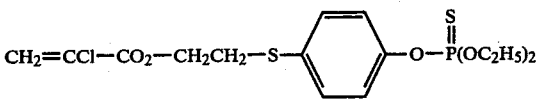

20. A compound of the formula:

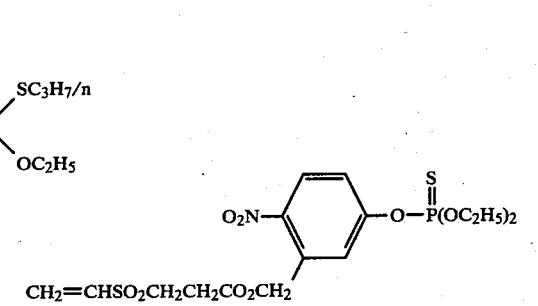

21. A compound of the formula:

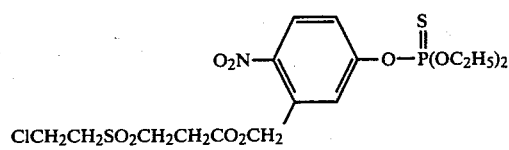

22. A compound of the formula:
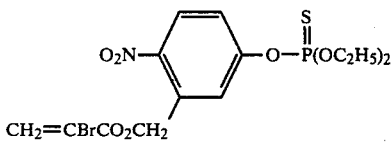
CH₂=CBrCO₂CH₂
23. A compound of the formula:
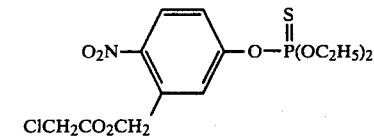
ClCH₂CO₂CH₂
24. A compound of the formula:
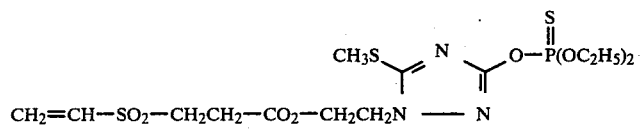
25. A compound of the formula:
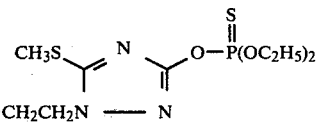
CH₂=CBr—CO₂—CH₂CH₂N——N
26. A compound of the formula:
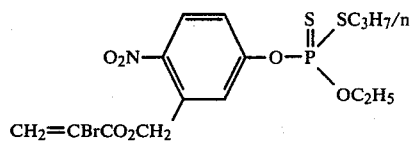
CH₂=CBrCO₂CH₂
27. A compound of the formula:
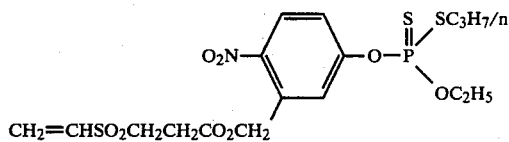
CH₂=CHSO₂CH₂CH₂CO₂CH₂
* * * * *